United States Patent
Overes et al.

(10) Patent No.: US 8,414,582 B2
(45) Date of Patent: Apr. 9, 2013

(54) INTRAMEDULLARY NAIL AND PROTRUDING SCREW LOCKING MECHANISM

(75) Inventors: Tom Overes, Langendorf (CH); Silas Zurschmiede, Grenchen (CH); Simone Volzer, Solothurn (CH); Robert Frigg, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 238 days.

(21) Appl. No.: 12/825,977

(22) Filed: Jun. 29, 2010

(65) Prior Publication Data
US 2011/0160729 A1    Jun. 30, 2011

Related U.S. Application Data

(60) Provisional application No. 61/222,234, filed on Jul. 1, 2009.

(51) Int. Cl.
*A61B 17/56* (2006.01)
*A61B 17/58* (2006.01)
*A61F 2/30* (2006.01)

(52) U.S. Cl.
USPC ............................................. 606/62; 606/64

(58) Field of Classification Search .............. 606/62–68, 606/250–251, 300–321, 329
See application file for complete search history.

(56) References Cited

U.S. PATENT DOCUMENTS

| 3,986,504 A | 10/1976 | Avila |
| 2008/0221577 A1* | 9/2008 | Elghazaly .................. 606/64 |

FOREIGN PATENT DOCUMENTS

| EP | 1685803 | 8/2006 |
| WO | 2004/100810 | 11/2004 |
| WO | 2008/141805 | 11/2008 |

* cited by examiner

*Primary Examiner* — Eduardo C. Robert
*Assistant Examiner* — Christina Negrellirodriguez
(74) *Attorney, Agent, or Firm* — Fay Kaplun & Marcin, LLP (57) ABSTRACT

An apparatus for treating a bone comprises an implant to be received within the bone, including a plurality of bores extending therethrough and a cavity formed therewithin, each of the bores being dimensioned to receive a bone fixation element and a plurality of inserts receivable in the cavity. Each insert includes an opening extending therethrough and configured to align with a corresponding bore. Each insert is movable between a resting configuration in which an opening width is smaller than a width of a bone fixation element inserted therethrough and a stressed configuration in which the opening width is expanded to a width greater than that of the bone fixation element in combination with a compression member movable into the cavity to apply a force moving the inserts from the resting configuration to the stressed configuration, withdrawal thereof reducing the force and permitting a return to the resting configuration.

19 Claims, 7 Drawing Sheets

INTRAMEDULLARY NAIL AND PROTRUDING SCREW LOCKING MECHANISM

PRIORITY CLAIM

The present application claims priority to U.S. Provisional Application Ser. No. 61/222,234 entitled "Intramedullary Nail and Protruding Screw Locking Mechanism" filed on Jul. 1, 2009 to Tom Overes, Silas Zurschmiede, Simone Volzer and Robert Frigg, the entire disclosure of which is incorporated herein by reference.

FIELD OF THE INVENTION

The present application is directed to the field of bone fixation and, more specifically, to a system and method for the fixation of bone fractures via an insertion of an intramedullary nail into the bone, the intramedullary nail being configured to receive bone screw therethrough in an operative configuration.

BACKGROUND INFORMATION

Intramedullary nails are used to stabilize and align fractured or otherwise damaged bones. Known procedures often employ bone screws inserted through the bone to engage an intramedullary nail at various angles relative to one another to stabilize the nail in the bone or to aid in stabilizing individual bone fragments. These bone screws are locked in place within the intramedullary nail via forced tapping into plastic or metal bushings. This may result in a loosening of the grip on the screws (e.g., when a screw is unthreaded from a previously tapped threading) and/or the creation of debris as the screws are tapped into the material of the bushing.

SUMMARY OF THE INVENTION

The present invention is directed to an apparatus for treating a bone, comprising an implant to be received within an interior of a bone, the implant including a plurality of cross bores extending therethrough and a cavity extending within the implant along at least a portion of a length thereof, each of the cross bores extending through the cavity and being dimensioned to receive therethrough a bone fixation element and a plurality of inserts slidably received in the cavity, each insert including an insert opening extending therethrough, the inserts being aligned within the cavity so that each insert opening aligns with a corresponding one of the cross bores, each insert being movable between a resting configuration in which a width of its insert opening is smaller than a width of a bone fixation element to be inserted through the corresponding cross bore and a stressed configuration in which the width of the insert opening is expanded to a width greater than that of the bone fixation element to be inserted through the corresponding cross bore in combination with a compression member movable into the cavity to apply a force to the inserts moving the inserts from the resting configuration to the stressed configuration, withdrawal of the compression member to reduce the force applied to the inserts permitting the inserts to return to resting configuration.

DETAILED DESCRIPTION

The present invention may be further understood with reference to the following description and the appended drawings, wherein like elements are referred to with the same reference numerals. The present invention relates generally to systems and methods for the fixation of fractured or otherwise damaged bone. Specifically, the invention relates to an intramedullary nail formed with a hollow cavity configured to receive at least one substantially cylindrical insert therein. The insert comprises an opening extending therethrough and configured to at least partially align with a bore extending perpendicularly through the intramedullary nail. Although, in a resting state, a width of the insert opening is smaller than a diameter of the bore, when the insert is compressed axially, a width of the insert opening expands to a size sufficient to permit a bone locking screw to be freely inserted therethrough. Thus, the exemplary intramedullary nail of the present invention permits a user to loosely insert at least one bone screw through at least an insert of the hollow cavity. After the bone screw has reached a desired position within the bone, the axial compression is withdrawn from the insert and the insert opening retracts to its resting state applying a radially constrictive pressure to the bone screw, thus locking a position thereof relative to the intramedullary nail and minimizing the problems associated with screws tapping into bushings described above.

Figure 1:
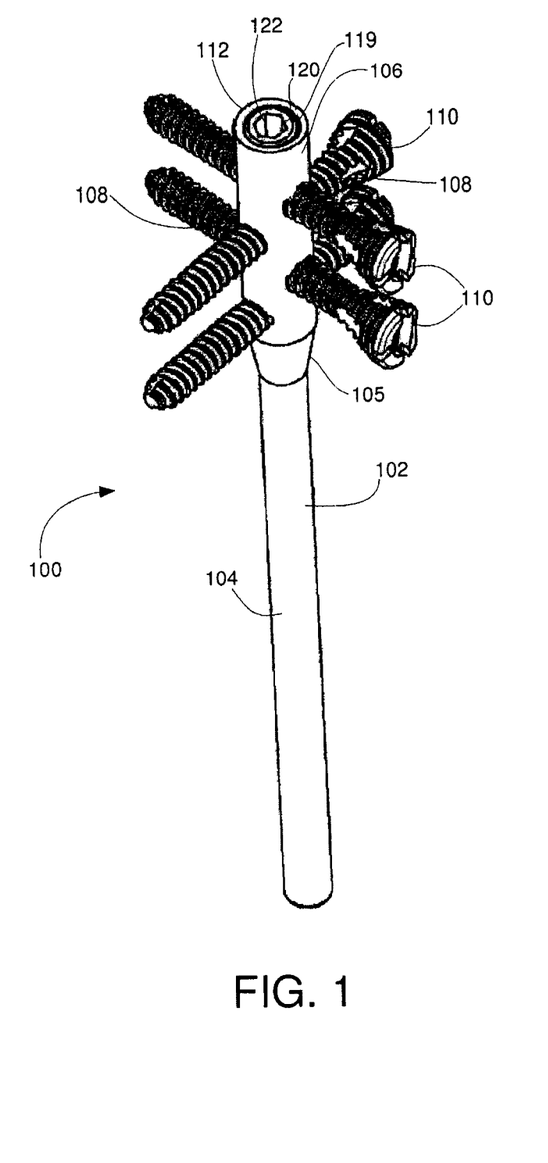
FIG. 1 shows a perspective view of an intramedullary nail according to a first embodiment of the invention.
Figure 2:
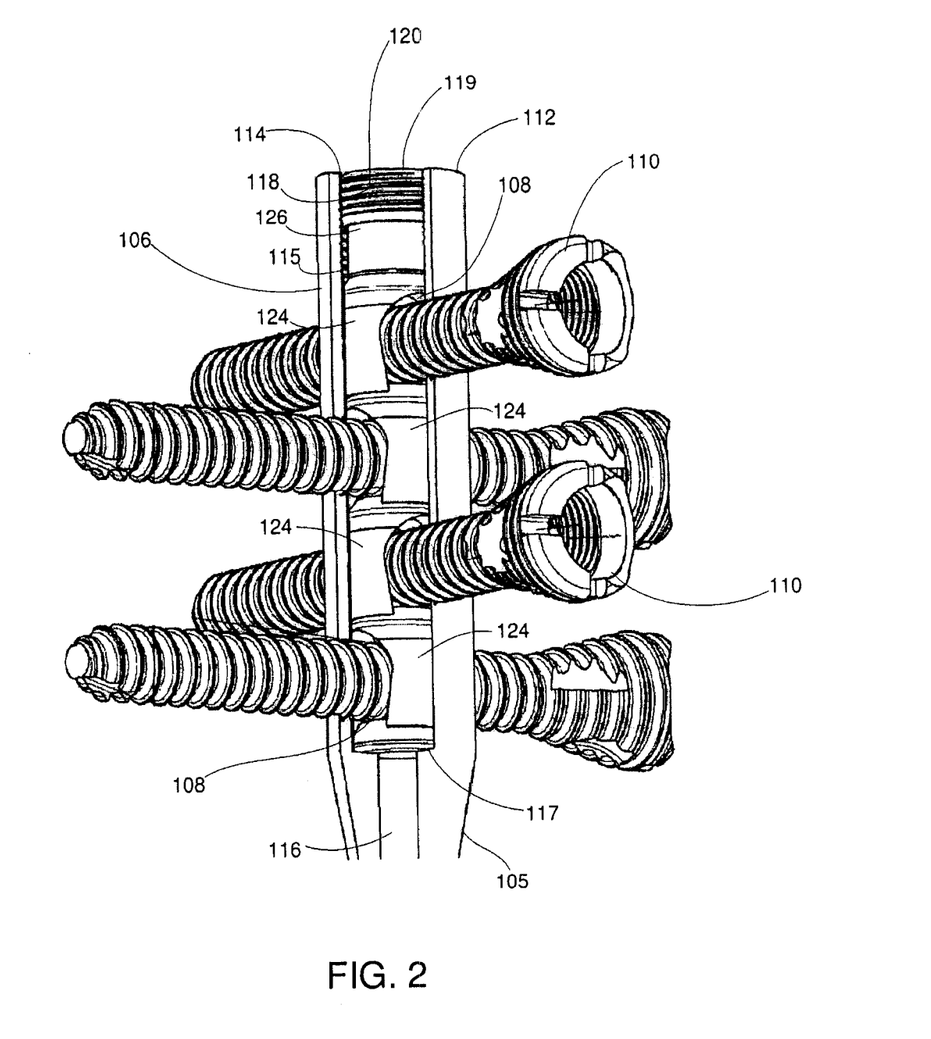
FIG. 2 shows a first partial cross-sectional view of the intramedullary nail of FIG. 1.
Figure 4:
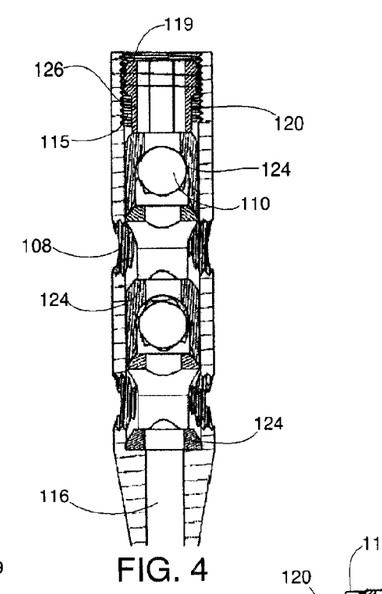
FIG. 4 shows a second partial cross-sectional view of the intramedullary nail of FIG. 1.

As shown in FIGS. 1-2, a system 100 according to an exemplary embodiment of the invention comprises an intramedullary nail 102 having an elongated shaft 104 extending from an increased diameter head 106 at a proximal end 112 and connected thereto by a tapered portion 105. As would be understood by those skilled in the art, dimensions of the elongated shaft 104 and the head 106 may be selected to conform to the requirements of a target bone fixation procedure. In an exemplary embodiment, an insert 124 is formed of Cobalt Chromium. Alternatively, the insert 124 may be formed of any material exhibiting a residual elasticity, as those skilled in the art will understand. A cavity 114 extends longitudinally into the head 106 from the proximal end 112 to a seat 117 at a distal end thereof. A plurality of cross bores 108 extend through the head 106 and the cavity 114. In this embodiment, an axis of each of the cross bores 108 is substantially perpendicular to a longitudinal axis of the intramedullary nail 102. The axes of the cross bores 108 may be distributed about the longitudinal axis of the intramedullary nail in any desired pattern. That is, the cross bores 108 may be distributed about the circumference of the head 106 in any desired pattern so long as they intersect the cavity 114. Each of the cross bores 108 is positioned at a location selected to receive a bone fixation element (e.g., a bone screw 110) to be mounted through the intramedullary nail 102. As shown in the partial cross-sectional view of FIG. 4, each of the bores 108 may comprise female threading with a pitch corresponding to a male threading of the bone screws 110. It is noted that although the embodiment of FIGS. 1-2 is shown with four bone screws 110 inserted through four substantially perpendicularly positioned cross bores 108, the cross bores 108 of the present invention may be positioned at any angles relative to one another without deviating from the spirit and scope of the present invention. Furthermore, the intramedullary nail 102 of the present invention may be provided with any number of bores 108 without deviating from the scope of the present invention. A reduced diameter cavity 116 may extend distally from the cavity 114 if desired to permit insertion of a Kirschner wire ("K-wire") through the intramedullary nail 102. Specifically, a K-wire (not shown) may be pre-implanted in a target portion of the bone prior to insertion of the intramedullary nail 102. The intramedullary nail 102 may be inserted into the bone so that the K-wire slides in from a distal opening of the reduced diameter cavity 116 adjacent the distal end of the shaft 104. Each of the inserts 124 may also comprise bores (not shown) extending therethrough, the bores being configured to permit slidable movement of the K-wire therepast. As those skilled in the art will understand, the K-wires may be removed from the intramedullary nail 102 prior to the insertion of bone screws 110 through the cross bores 108. In an exemplary embodiment of the present invention, the intramedullary nail 102 and the bone screws 110 are formed of titanium or a titanium alloy, although other materials may be employed without deviating from the scope of the present invention.

As shown more clearly in the partial cross-sectional view of FIG. 2, the cavity 114 extends substantially parallel to a longitudinal axis of the intramedullary nail 102 and is open to each of the bores 108. A portion of the cavity 114 adjacent to the proximal end 112 is formed with female threading 115 with a predetermined pitch corresponding to a male threaded portion 118 of a bolt 120 to be inserted therein. As shown in FIG. 2, the female threading 115 extends into the cavity 114 by a predetermined distance. The bolt 120 may further comprise a driver connection 122 configured to engage a driving instrument to permit the insertion thereof into the cavity 114, as those skilled in the art will understand. The driver connection 122 may be a hexagonal socket, a torx drive, or any other suitable drive. The bolt 120 which further comprises a nonthreaded shaft portion 126 configured to be slidably received in the cavity 114 to abut a proximal-most one of a plurality of inserts 124 slidably received in the cavity 114 may also be formed of one of titanium, a titanium alloy, cobalt chromium or any other suitable material.

Figure 3:
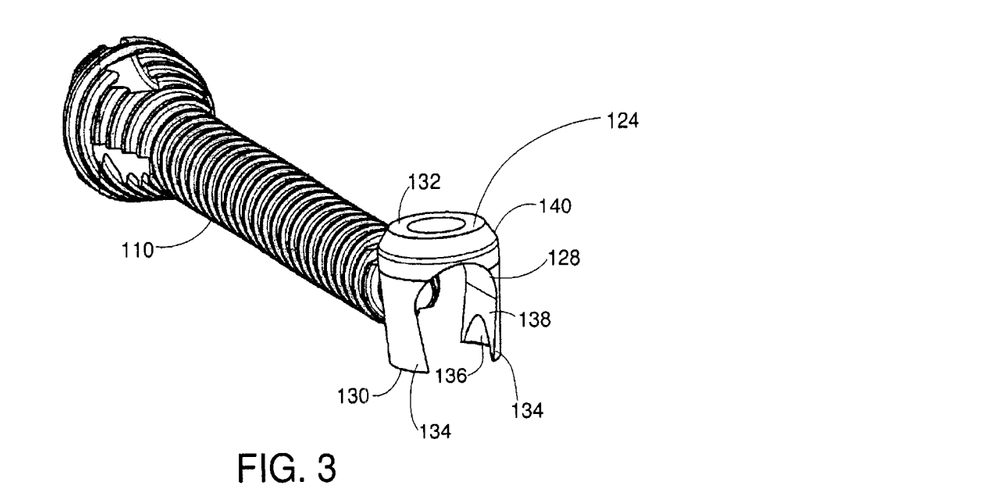
FIG. 3 shows a perspective view of an exemplary insert of FIG. 1.

Each insert 124 is biased toward a resting shape substantially conforming to a shape of the cavity 114 with a clearance between a radially outer surface of the insert 124 and an inner wall of the cavity 114 to permit expansion of the insert 124 as will be described in more detail below. If desired, the shape of each of the inserts 124 may be selected so that they may be received in the cavity 114 only in an orientation with respect to the longitudinal axis of the intramedullary nail 102 in which the opening 128 thereof will align with a corresponding cross bore 108. Each insert 124 includes a proximal abutting surface 132 and distal abutting surfaces 130 which engage adjacent ones of the inserts 124 except that the proximal abutting surface 132 of the proximal-most one of the inserts 124 abuts the distal end of the bolt 120 and the distal surfaces 130 of the distal-most one of the inserts 124 abuts the seat 117 of the cavity 114. Each insert 124 includes a pair of arms 134 separated from one another by an arced opening 128 extending from a distal end of the insert 124 to a distal face of the proximal abutting surface. Dimensions of the opening 128 are selected to be smaller than a diameter of a bone screw 110 to be inserted therethrough so that, when the insert 124 is in a first unstressed configuration, the bone screw 110 is prevented from being inserted therethrough. Each of the arms 134 includes a cutout 136 on a radially inner wall thereof adjacent the distal abutting surface 130 thereof for receiving the proximal end of an adjacent insert 124 as will be described in more detail below. Furthermore, a width of the opening 128 decreases as the distal abutting surfaces 130 are approached, aiding in longitudinal compression of the insert 124, as will be described in greater detail hereinafter. A chamfer 140 is formed between the proximal ends of the arms 134 and the proximal abutting surface 132 which has a diameter smaller than that of the arms 134. The arms 134 extend distally at a substantially constant diameter so that the distal abutting surfaces 130 of one insert 124 contact the chamfer 140 of the distally adjacent insert 124. The cutouts 136 provide clearance for the radially outer end of the proximal abutting surface 132 of the adjacent insert 124 so that the arms 134 contact the angled chamfer at the angled surface formed by the cutouts 136 when the inserts 124 are stacked atop one another in the cavity 114 with the distal abutting surfaces 134 of one insert 124 resting on the proximal abutting surface 132 of an adjacent insert 124. A taper angle of the chamfer 140 is selected to provide a desired degree of radial expansion of the opening 128 as the arms 134 move distally over the chamfer 140 and are spread radially apart from one another. Specifically, when the bolt 120 is turned to force the bolt 120 further distally into the cavity 114, the proximal-most insert 124 is compressed axially against the adjacent insert 124 sliding the arms 134 thereof distally over the chamfer 140 of the adjacent insert 124 and expanding the opening 128 to a size selected to facilitate the free insertion of a bone screw 110 thereinto. This axial force is transmitted from each insert 124 to the distally adjacent insert 124 expanding all of the openings 128 to the desired size. The bone screws 110 may then be inserted as would be understood by those skilled in the art. A steeper angle of the chamfer 140 is directly related to an increased pivotal distance that the chamfer 140 must travel before expanding the opening 128 to the desired size. Furthermore, the combination of a low pitch of the threaded portion 118 of the bolt 120 and a steep angle of the chamfer 140 results in an axial force multiplication, wherein the threads and the chamfer 140 proportionally increase a magnitude of the axially applied force, as those skilled in the art will understand. The increased magnitude of the axially applied force permits the use of a substantially stiff material for the inserts 124, so that the material will be sufficiently rigid to withstand forces applied thereto during and after insertion into a target portion of bone while permitting the temporary deformation required to facilitate insertion of the bone screws 110.

In accordance with an exemplary method of use of the system 100, a plurality of inserts 124 are inserted into the cavity 114 with an axis of each of the openings 128 aligned with an axis of a corresponding one of the cross bores 108. The bolt 120 is then screwed into the cavity 114 until a top surface thereof extends into the cavity 114 by a predetermined distance, as shown in the partial cross-sectional view of FIGS. 4 and 5. As described above, the driving of the bolt 120 distally into the cavity 114 exerts an axial force on a first one of the inserts 124 located adjacent thereto which force is transmitted to the rest of the inserts 124 in turn. Those skilled in the art will understand that, the steps for the expansion of the openings 128 may be performed before or after the intramedullary nail 102 has been inserted into the body using any known technique. Furthermore, in an alternate embodiment, the movement of the bolt 120 into the cavity 114 may be offset from the longitudinal axis of the intramedullary nail 102 so long as the force applied thereby against the first insert 124 is translated into an axially compressive force (e.g., through the movement of the bolt 120 laterally against the chamfer 140 to redirect the force distally. Specifically, the bolt 120 may be inserted over the first one of the inserts at an angle deflected from a longitudinal axis of the cavity 114 by up to 90°. It is further noted that the pitch of the threaded portion 118 of the bolt 120 may be selected to conform to the amount of axial displacement desired, wherein a lower pitch corresponds to a increased axial force applied to the inserts 124 for a certain rotational movement, as those skilled in the art will understand. The axial force applied to the first adjacent insert 124 then causes the same axial compression and radial expansion of the arms 134 described above.

Figure 5:
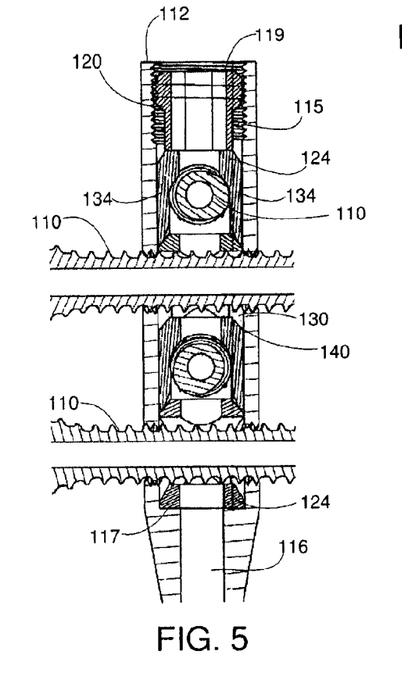
FIG. 5 shows a third partial cross-sectional view of the intramedullary nail of FIG. 1.
Figure 6:
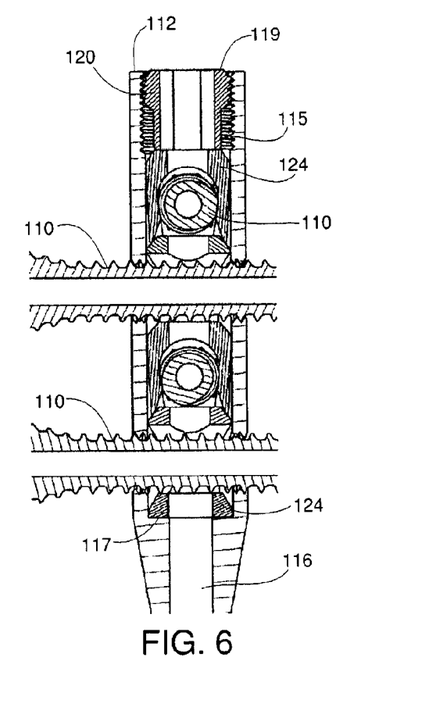
FIG. 6 shows a fourth partial cross-sectional view of the intramedullary nail of FIG. 1.

As shown in FIG. 5, the radial expansion of the insert 124 causes each of the openings 128 to assume dimensions large enough to permit insertion of shafts 111 of the bone screws 110 therethrough with a minimal amount of friction therebetween while still preventing heads 113 of the bone screws 110 from being inserted thereinto. The bone screws 110 may then be inserted into the cross bores 108 using any known technique. Once each of the bone screws 110 has been inserted to a target location within the cross bores 108 and inserts 124, the bolt 120 is rotated (e.g., counter-clockwise) to move the bolt 120 proximally out of the cavity 114 gradually reducing the axially compressive forces applied to the inserts 124. In a preferred embodiment, the bolt 120 is retracted to a position wherein a first end 119 of the bolt 120 lies substantially flush against the proximal end 112 of the intramedullary nail 102. Reduction of the axially compressive force applied to the inserts 124 permits the inserts 124 to return to their initial non-stressed configurations with the arms 134 moving radially inward against the bone screws 110 gripping the bone screws 110 and locking them in place. The inserts 124 are preferably formed of a material which, when compressed to receive a bone screw 110, is elastically deformed so that the process may be repeated (e.g., if it is necessary to withdraw and reinsert bone screws 110 for any reason) without compromising the efficacy of the inserts 124. Because each of the bone screws 110 of the present invention is locked independent of other bone screws, a user may optionally use only a number of bone screws 110 called for in a particular procedure. That is, a user of not required to employ as many bone screws 110 as there are cross bores 108. For example, in the embodiment of FIGS. 1-6, a user may optionally use less than four bone screws 110 without compromising the strength of the frictional engagement on each of the bone screws 110.

Figure 7:
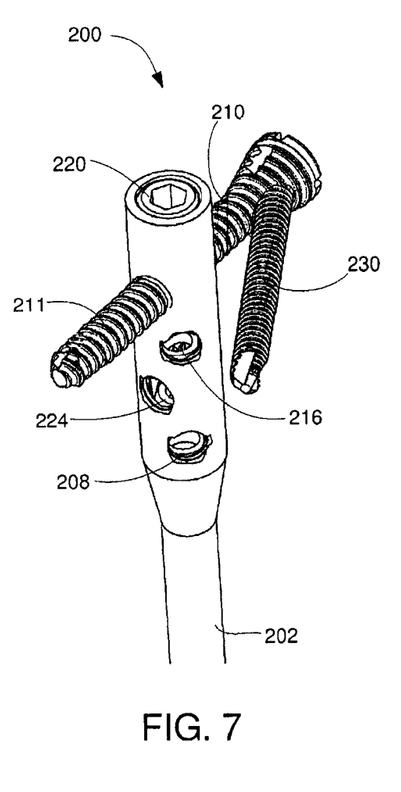
FIG. 7 shows a first perspective view of an intramedullary nail according to a second exemplary embodiment of the present invention.
Figure 8:
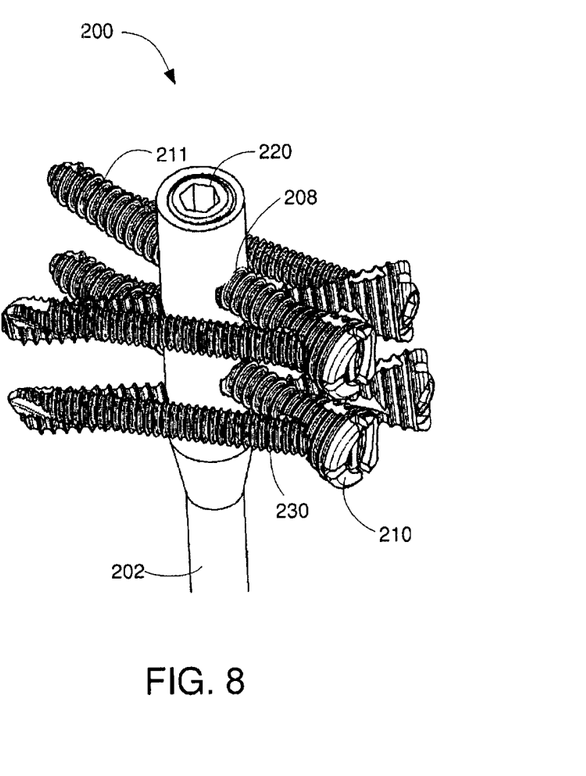
FIG. 8 shows a second perspective view of the intramedullary nail of FIG. 7.

As shown in FIGS. 7 and 8, a system 200 according to another embodiment of the invention is formed substantially similarly as the system 100 except that an angle of each of a plurality of cross bores 208 with respect to a longitudinal axis of an intramedullary nail 202 is varied. Furthermore, first bone screws 210 of the system 200 are configured to permit screw-in-screw insertion, as those skilled in the art will understand. The exemplary system 200 may be employed, for example, in the proximal humerus where the employment of first bone screws 210 at a plurality of angles finds particular benefit. The cross bores 208 may be threaded with a female threading corresponding to a male threading of shafts 211 of each of the bone screws 210. Furthermore, inserts 224 of the system 200 are configured with openings (not shown) that extend therethrough at angles corresponding to the angles of the respective ones of the cross bores 208 so that, when the inserts 224 are stacked within a cavity 216 of an intramedullary nail 202, axes of the openings (not shown) align with axes of the respective ones of the cross bores 208. The first bone screws 210 may each comprise a bore 212 configured to receive a respective second bone screw 230 therethrough. Specifically, whereas the first bone screws 210 are configured to be inserted and locked within a respective cross bore 208 of the intramedullary nail 202, the second bone screws 230 are configured to engage the first bone screws 210 at any appropriate angle to provide an additional locking strength to the system 200.

Figure 9:
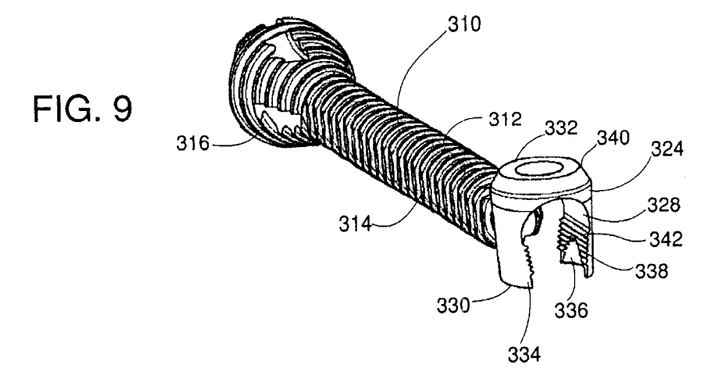
FIG. 9 shows an insert and bone screw according to a third alternate embodiment of the present invention.

Various modifications may be made to the inserts and bone screws of the present invention including, but not limited to the embodiments shown in FIGS. 9-14. Specifically, FIG. 9 depicts an insert 324 engageable with a bone screw 310. The insert 324 is formed substantially similarly to the insert 124 of FIGS. 1-6, comprising a substantially cylindrical body with an opening 328 extending therethrough to define first and second arms 334. A cutout 336 located on an inner wall of the insert 324 is located adjacent to and open to a distal end 330 while a taper 340 extends to a proximal end 332. The insert 324 differs from the insert 124 in that a frictionally contacting surface 338 thereof is provided with multiple teeth 342 that extend into the opening 328 at a predetermined taper angle. The teeth 342 only extend along a predetermined portion of the contacting surface 338 configured to engage a shaft 312 of the bone screw 310 in an operative configuration. The shaft of the bone screw 310 is provided with two opposing flattened walls 314 configured to engage the teeth 342. Specifically, once the bone screw 310 has been inserted through the radially expanded insert 324, as described in greater detail with respect to FIGS. 1-6, release of the axially compressive force on the inserts 324 allows the aims 334 to retract radially inward over the outer wall of the shaft 312. The teeth 342 then apply a radially constrictive pressure against the flattened walls 314 locking a position of the screw 310 with respect to the intramedullary nail (not shown). Those skilled in the art will understand that engagement of the teeth 342 with the threads of the shaft 312 increases a frictional locking force between the insert 324 and the bone screw 310. It is further noted that although teeth 342 are described in the present embodiments, the insert 324 may optionally be provided with any type of a roughened or treated surface to increase friction without deviating from the scope of the present invention.

The bone screw 310 may also be employed in place of the bone screw 210 of FIGS. 7-8, wherein the flattened walls 314 will ensure that the bone screw 310 is inserted into the insert 224 in a predetermined orientation with the flattened walls 314 engaging the contacting surfaces of the inner walls of the insert 224. In this manner, a surgeon or other user can ensure that the second bone screw 230 assumes a predetermined position when inserted into the bone screw 310 and also prevent screw collisions, as those skilled in the art will understand.

Figure 10:
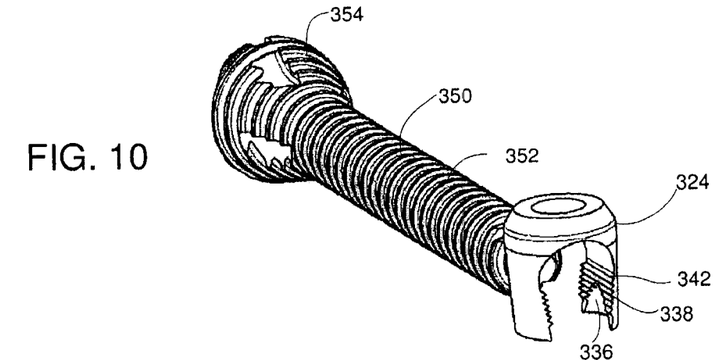
FIG. 10 shows an insert and bone screw according to a fourth alternate embodiment of the present invention.
Figure 11:
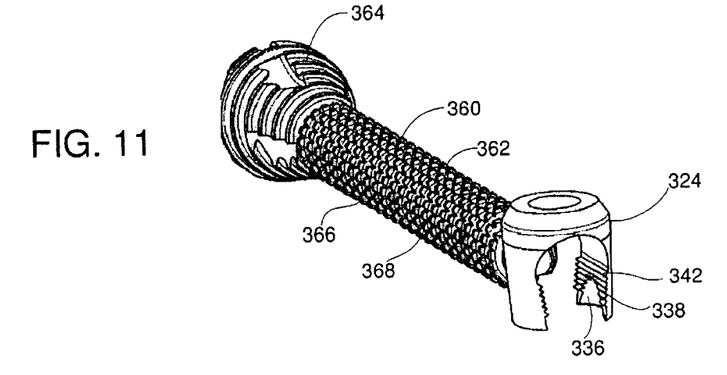
FIG. 11 shows an insert and bone screw according to a fifth alternate embodiment of the present invention.

In another embodiment of the present invention, as shown in FIG. 10, the insert 324 is configured to engage a standard bone screw 350 comprising a shaft 352 extending from an increased diameter head 354, wherein the shaft 352 comprises a substantially circular cross-section. Engagement of the teeth 342 of the insert 324 with the threads of the shaft 352 is facilitated in the same manner discussed above. In yet another embodiment, as shown in FIG. 11, the insert 324 may be configured to engage a bone screw 360 having a shaft 362 and an increased diameter head 364. The shaft 362 comprises threads 366 extending substantially helically around the shaft 352, as those skilled in the art will understand. The shaft 362 is further provided with a plurality of transverse cuts 368 extending substantially parallel to a longitudinal axis of the bone screw 360, the transverse cuts 368 defining a plurality of engagement portions to facilitate engagement with the teeth 342 of the insert 324. Specifically, dimensions of a space between adjacent ones of the transverse cuts 368 is selected such that the teeth 342 can be received within each of the transverse cuts 368 to provide a form fit engagement in addition to a frictional engagement of the teeth 342 with the shaft 362, as those skilled in the art will understand.

Figure 12:
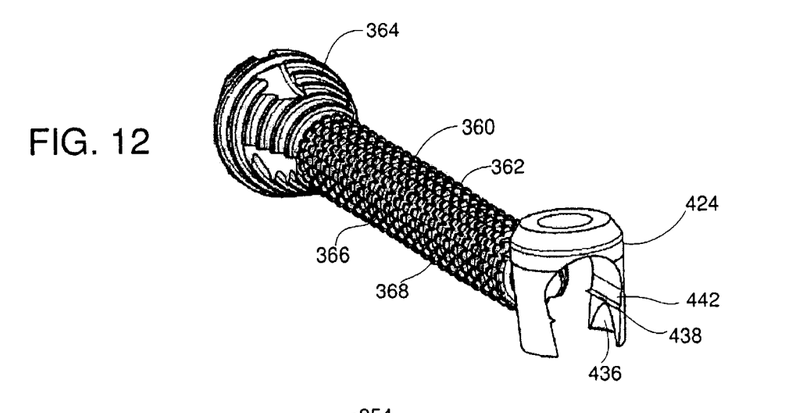
FIG. 12 shows an insert and bone screw according to a sixth alternate embodiment of the present invention.

FIG. 12 depicts yet another embodiment of the present invention wherein an insert 424 is formed substantially similarly as the insert 324 of FIGS. 9-11 with the exception of the teeth 342. Specifically, the insert 424 is provided with a single ridge 442 extending out of a frictionally contacting surface 438 thereof. The ridge 442 may extend substantially perpendicularly into the insert 424 or, in an alternate embodiment, may be angled relative thereto. The ridge 442 is configured to engage a transverse cut formed in the shaft 362 of the bone screw 360 by one of the transverse cuts 368, as described in greater detail above.

Figure 13:
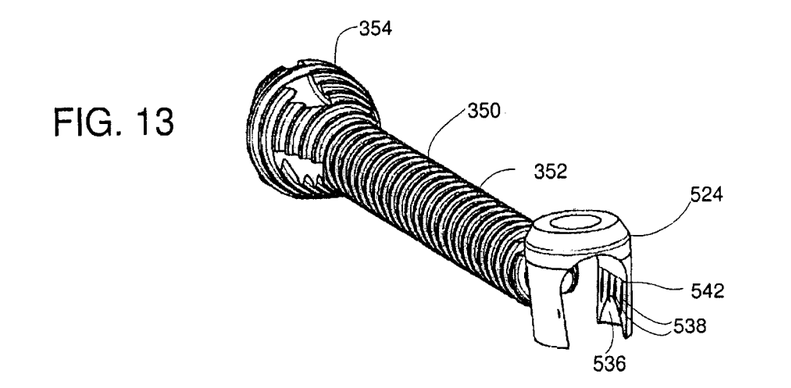
FIG. 13 shows an insert and bone screw according to a seventh alternate embodiment of the present invention.

FIG. 13 depicts yet another embodiment of the present invention, wherein an insert 524 is formed substantially similarly as the insert 124 of FIGS. 1-6 with the exception of a female threaded portion 542 formed on a contacting surface 538 of an inner wall of the insert 524. The threaded portion 542 is formed with a predetermined pitch configured to engage threads of the threaded shaft 352.

Figure 14:
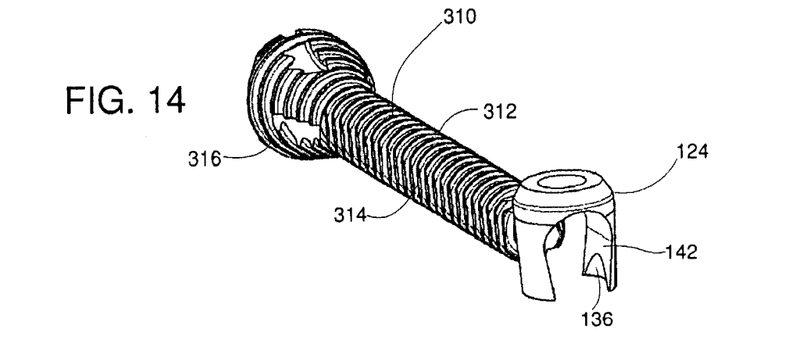
FIG. 14 shows an insert and bone screw according to an eighth alternate embodiment of the present invention.

FIG. 14 depicts yet another embodiment of the present invention, wherein the insert 124 is configured to engage the bone screw 310 described in greater detail earlier with respect to FIG. 9. Specifically, the insert 124 is operated in the same manner discussed above to engage the flattened wall 314 of the bone screw 310.

In an alternate embodiment of the present invention, each of the elements of the present invention may be formed of any suitable material including, but not limited to a plastic, stainless steel or another biocompatible material. Furthermore, additional or lesser inserts 124 and respective cross bores 108 of the intramedullary nail 102 may be employed without deviating from the scope of the present invention. Still further, although embodiments of the present invention depict the use of multiple inserts formed with the same dimensions, the dimensions of each of the inserts and respective openings as well as the dimensions of each of the bone screws used in any particular procedure may be modified without deviating from the scope of the present invention. It is further noted that embodiments of the present invention may also be employed in any prosthesis with a shaft or elongating shaft such as, for example, hip prostheses and knee prostheses. Furthermore, embodiments of the present invention may be employed in tibial nails, femoral nails, humeral nails, etc. without deviating from the scope of the present invention. In another embodiment (not shown), the dimensions of the inserts may be modified to permit insertion in a hole extending through a bone plate instead of a nail It will be apparent to those skilled in the art that various other modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. An apparatus for treating a bone, comprising:
an implant to be received within an interior of a bone, the implant including a plurality of cross bores extending therethrough and a cavity extending within the implant along at least a portion of a length thereof, each of the cross bores extending through the cavity and being dimensioned to receive therethrough a bone fixation element;
a plurality of inserts slidably received in the cavity, each insert including an insert opening extending therethrough, the inserts being aligned within the cavity so that each insert opening aligns with a corresponding one of the cross bores, each insert being movable radially between a resting configuration in which a width of its insert opening is smaller than a width of a bone fixation element to be inserted through the corresponding cross bore and a stressed configuration in which the width of the insert opening is expanded to a width greater than that of the bone fixation element to be inserted through the corresponding cross bore; and
a compression member movable into the cavity to apply a force to the inserts moving the inserts from the resting configuration to the stressed configuration, withdrawal of the compression member to reduce the force applied to the inserts permitting the inserts to return to resting configuration.

2. The apparatus of claim 1, wherein the inserts are stacked on one another within the cavity and wherein the compression member comprises a bolt insertable into a proximal end of the cavity to apply a compressive force to a proximal-most one of the inserts, the compressive force being transmitted from one insert to another through the stack.

3. The apparatus of claim 1, wherein an inner contacting surface of the opening of first one of the inserts includes a friction enhancing element to permit locking engagement with an outer surface of a bone fixation element to be inserted through the corresponding cross bore.

4. The apparatus of claim 3, further comprising a cutout formed on the inner contacting surface to increase frictional engagement between the insert and a bone fixation element to be inserted through the corresponding cross bore.

5. The apparatus of claim 3, wherein the friction enhancing element is one of a ridge, a cutout, a plurality of teeth and female threading.

6. The apparatus of claim 1, wherein a proximal end of a first one of the inserts comprises a tapered surface angled with respect to a longitudinal axis of the implant and a distal end of a second one of the inserts proximally adjacent thereto includes a pair of arms separated from one another by the corresponding insert opening, distal ends of the arms of the second insert engaging the tapered surface of the first insert so that, when moved distally over the tapered surface of the first insert, the arms of the second insert are spread radially apart from one another increasing a width of the opening.

7. The apparatus of claim 1, wherein each of the inserts includes a pair of distally extending arms separated from one another by the corresponding insert opening.

8. The apparatus of claim 6, wherein the insert is formed of a material selected so that deformation thereof between the resting and stressed configurations is elastic.

9. The apparatus of claim 1, wherein the insert is formed of Cobalt Chromium.

10. The apparatus of claim 1, wherein the cross bore is threaded.

11. The apparatus of claim 1, wherein each of the inserts is keyed to a shape of the cavity so that the inserts may be inserted thereinto only in an orientation in which the insert openings are aligned with the corresponding cross bores.

12. A system for treating a bone, comprising:
   an implant to be received within an interior of a bone, the implant including a plurality of cross bores extending therethrough and a cavity extending within the implant along at least a portion of a length thereof, each of the cross bores extending through the cavity;
   a plurality of bone fixation elements, each of the bone fixation elements being dimensioned for insertion through a corresponding one of the cross bores;
   a plurality of inserts slidably received in the cavity, each insert including an insert opening extending therethrough, the inserts being aligned within the cavity so that each insert opening aligns with a corresponding one of the cross bores, each insert being movable radially between a resting configuration in which a width of its insert opening is smaller than a width of the bone fixation element to be inserted through the corresponding cross bore and a stressed configuration in which the width of the insert opening is expanded to a width greater than that of the bone fixation element to be inserted through the corresponding cross bore; and
   a compression member movable into the cavity to apply a force to the inserts moving the inserts from the resting configuration to the stressed configuration, withdrawal of the compression member to reduce the force applied to the inserts permitting the inserts to return to resting configuration to grip the bone fixation elements received therein.

13. The system of claim 12, wherein a first one of the bone fixation elements comprises opposing flattened walls extending along at least a portion of a length thereof.

14. The system of claim 12, wherein a second one of the bone fixation elements is threaded.

15. The system of claim 14, wherein the second bone fixation element comprises a plurality of transverse grooves extending substantially parallel to a longitudinal axis of a shaft thereof.

16. The system of claim 14, wherein the second bone fixation element further comprises a bore extending through a portion thereof to permit insertion of a bone fixation screw therethrough.

17. A method for readjusting a bone fixation element in a bone plate, comprising:
   inserting a bone fixation element into a hole extending through a bone plate and into a target portion of bone, the bone fixation element comprising a cavity extending thereinto from a first free end to a second end and a cross bore extending through a portion of the bone fixation element comprising the cavity;
   inserting a bolt into the first free end of the cavity, insertion of the bolt applying a compressive force to an insert received within the cavity, wherein the an opening extending through the insert is aligned with the cross bore and insertion of the bolt causes the insert to move from a first unstressed configuration wherein dimensions of the opening are smaller than dimensions of the cross bore to a second stressed configuration wherein dimensions of the opening are increased to the dimensions of the cross bore;
   inserting a first bone fixation device through the cross bore so that it passes through the opening of the insert and out of an opposite end of the cross bore; and
   loosening the bolt so that the insert is permitted to return to the first unstressed configuration, causing the insert to apply a radially constrictive pressure on the first bone fixation device to lock a position thereof.

18. The method of claim 17, wherein movement of the insert to the second stressed configuration causes a longitudinal compression and radial expansion thereof.

19. The method of claim 17, further comprising the step of inserting a second bone fixation device through a bore formed in the first bone fixation device.

* * * * *